United States Patent
Kuwahara

(10) Patent No.: US 11,359,240 B2
(45) Date of Patent: Jun. 14, 2022

(54) METHOD FOR DETECTING TARGET MOLECULE IN WHICH ROLLING CIRCLE AMPLIFICATION IS USED

(71) Applicant: National University Corporation Gunma University, Gunma (JP)

(72) Inventor: Masayasu Kuwahara, Gunma (JP)

(73) Assignee: National University Corporation Gunma University, Gunma (JP)

( * ) Notice: Subject to any disclaimer, the term of this patent is extended or adjusted under 35 U.S.C. 154(b) by 350 days.

(21) Appl. No.: 16/494,121

(22) PCT Filed: Mar. 14, 2018

(86) PCT No.: PCT/JP2018/009874
§ 371 (c)(1),
(2) Date: Sep. 13, 2019

(87) PCT Pub. No.: WO2018/168895
PCT Pub. Date: Sep. 20, 2018

(65) Prior Publication Data
US 2020/0071759 A1 Mar. 5, 2020

(30) Foreign Application Priority Data
Mar. 15, 2017 (JP) .............................. JP2017-050620

(51) Int. Cl.
*C12Q 1/6876* (2018.01)
*C12N 15/115* (2010.01)
(Continued)

(52) U.S. Cl.
CPC ......... *C12Q 1/6876* (2013.01); *C07D 277/66* (2013.01); *C12N 15/115* (2013.01); *C12Q 1/6844* (2013.01)

(58) Field of Classification Search
CPC ........ C12Q 2525/205; C12Q 2531/125; C12Q 15/115
See application file for complete search history.

(56) References Cited

U.S. PATENT DOCUMENTS

2019/0040465 A1 2/2019 Kuwahara

FOREIGN PATENT DOCUMENTS

| CN | 104764774 A | 7/2015 |
| JP | 2012-080871 A | 4/2012 |
(Continued)

OTHER PUBLICATIONS

Search Report in International Application No. PCT/JP2018/009874 dated Jun. 12, 2018, 2 pages.
(Continued)

*Primary Examiner* — Teresa E Strzelecka
(74) *Attorney, Agent, or Firm* — Marshall, Gerstein & Borun LLP

(57) ABSTRACT

A method of detecting a target molecule, the method comprising: forming a complex of a target molecule, a capture oligonucleotide, an oligonucleotide primer, and a single-stranded circular DNA; performing a nucleic acid amplification reaction by rolling circle amplification based on the formation of the complex; and detecting amplified nucleic acid; wherein the single-stranded circular DNA contains a first region, and a second region linked to the 3'-side of the first region, and preferably further contains a sequence complementary to a detection reagent-binding sequence; the primer contains a first aptamer sequence which binds to the target molecule, and a sequence which is linked to the 3'-side of the first aptamer sequence and is complementary to the first region of the single-stranded circular DNA; and the capture oligonucleotide contains a sequence complementary to the second region of the single-stranded circular DNA,
(Continued)

and a second aptamer sequence which is linked to the 3'-side of the sequence complementary to the second region and binds to the target molecule.

18 Claims, 9 Drawing Sheets

Specification includes a Sequence Listing.

(51) Int. Cl.
    *C12Q 1/6844*     (2018.01)
    *C07D 277/66*     (2006.01)

(56) References Cited

FOREIGN PATENT DOCUMENTS

| WO | WO-2006/086669 A2 | 8/2006 |
| WO | WO-2016/152936 A1 | 9/2016 |
| WO | WO-2016/205940 A1 | 12/2016 |

OTHER PUBLICATIONS

International Preliminary Report on Patentability in International Application No. PCT/JP2018/009874 dated Aug. 7, 2019, 6 pages.
Fujita et al., "Specific Light-Up System for Protein and Metabolite Targets Triggered by Initiation Complex Formation", Scientific Reports, vol. 7, Nov. 9, 2017, 8 pages.
Guo et al., "Label-free and Highly Sensitive Electrochemical Detection of E. coli Based on Rolling Circle Amplifications Coupled Peroxidase-mimicking DNAzyme Amplification", Biosensors and Bioelectronics, vol. 75, Jan. 15, 2016, pp. 315-319.
Fujita et al., "Novel One-Tube-One-Step Real-Time Methodology for Rapid Transcriptomic Biomarker Detection: Signal Amplification by Ternary Initiation Complexes", Analytical Chemistry, vol. 88, 2016, pp. 7137-7144.
Extended European Search Report in EP Application No. 18767582.2 dated Nov. 11, 2020, 5 pages.

SEQUENCE LISTING

<160> NUMBER OF SEQ ID NOS: 17

<210> SEQ ID NO 1
<211> LENGTH: 22

```
<212> TYPE: DNA
<213> ORGANISM: Artificial Sequence
<220> FEATURE:
<223> OTHER INFORMATION: oligonucleotide

<400> SEQUENCE: 1
agggttaggg ttagggttag gg                                              22

<210> SEQ ID NO 2
<211> LENGTH: 22
<212> TYPE: DNA
<213> ORGANISM: Artificial Sequence
<220> FEATURE:
<223> OTHER INFORMATION: oligonucleotide

<400> SEQUENCE: 2
agggagggcg ctgggaggag gg                                              22

<210> SEQ ID NO 3
<211> LENGTH: 26
<212> TYPE: DNA
<213> ORGANISM: Artificial Sequence
<220> FEATURE:
<223> OTHER INFORMATION: oligonucleotide

<400> SEQUENCE: 3
ttagggttag ggttagggtt agggtt                                          26

<210> SEQ ID NO 4
<211> LENGTH: 27
<212> TYPE: DNA
<213> ORGANISM: Artificial Sequence
<220> FEATURE:
<223> OTHER INFORMATION: oligonucleotide

<400> SEQUENCE: 4
tggggagggt ggggagggtg gggaagg                                         27

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gggcggcggg ctgggcgggg                                                 20

<210> SEQ ID NO 6
<211> LENGTH: 18
<212> TYPE: RNA
<213> ORGANISM: Artificial Sequence
<220> FEATURE:
<223> OTHER INFORMATION: oligonucleotide

<400> SEQUENCE: 6
gggaggggcg ggucuggg                                                   18

<210> SEQ ID NO 7
<211> LENGTH: 18
<212> TYPE: DNA
<213> ORGANISM: Artificial Sequence
<220> FEATURE:
<223> OTHER INFORMATION: DNA primer 1

<400> SEQUENCE: 7
```

```
gaagctgttg ttatcact                                                  18

<210> SEQ ID NO 8
<211> LENGTH: 30
<212> TYPE: DNA
<213> ORGANISM: Artificial Sequence
<220> FEATURE:
<223> OTHER INFORMATION: Positive control primer

<400> SEQUENCE: 8
agctcctttt ttgggacttt tcttcttcga                                     30

<210> SEQ ID NO 9
<211> LENGTH: 31
<212> TYPE: DNA
<213> ORGANISM: Artificial Sequence
<220> FEATURE:
<223> OTHER INFORMATION: Capture probe 1

<400> SEQUENCE: 9
aaaggagaac ctcaagctcc tttggttggt g                                   31

<210> SEQ ID NO 10
<211> LENGTH: 37
<212> TYPE: DNA
<213> ORGANISM: Artificial Sequence
<220> FEATURE:
<223> OTHER INFORMATION: Capture probe 2

<400> SEQUENCE: 10
aaaggagaac ctcaagctcc ggcaccacgg ucggauc                             37

<210> SEQ ID NO 11
<211> LENGTH: 17
<212> TYPE: DNA
<213> ORGANISM: Artificial Sequence
<220> FEATURE:
<223> OTHER INFORMATION: Detection probe 1

<400> SEQUENCE: 11
tggttggaaa tttttg                                                    17

<210> SEQ ID NO 12
<211> LENGTH: 28
<212> TYPE: DNA
<213> ORGANISM: Artificial Sequence
<220> FEATURE:
<223> OTHER INFORMATION: Detection probe 2

<400> SEQUENCE: 12
gaucgcauuu ggacuucugc cttttttg                                       28

<210> SEQ ID NO 13
<211> LENGTH: 62
<212> TYPE: DNA
<213> ORGANISM: Artificial Sequence
<220> FEATURE:
<223> OTHER INFORMATION: DNA template 1

<400> SEQUENCE: 13
cccaacccta cccaccctca agaaaaaaaa gtgataattg ttgtcgaaga agaaaaaaaa    60
tt                                                                   62

<210> SEQ ID NO 14
<211> LENGTH: 67
```

```
<212> TYPE: DNA
<213> ORGANISM: Artificial Sequence
<220> FEATURE:
<223> OTHER INFORMATION: DNA template 2

<400> SEQUENCE: 14
cccaaaaaag gagcttgagg ttctccttta aaaagaagct gttgtattgt tgtcgaagaa      60
gaaaagt                                                                67

<210> SEQ ID NO 15
<211> LENGTH: 54
<212> TYPE: DNA
<213> ORGANISM: Artificial Sequence
<220> FEATURE:
<223> OTHER INFORMATION: sequence extended from the detection probe (5'
      part)

<400> SEQUENCE: 15
tggttggaaa tttttggga cttttcttct tcgacaacaa tacaacagct tctt             54

<210> SEQ ID NO 16
<211> LENGTH: 36
<212> TYPE: DNA
<213> ORGANISM: Artificial Sequence
<220> FEATURE:
<223> OTHER INFORMATION: sequence extended from the detection probe (3'
      part)

<400> SEQUENCE: 16
gactttcctt cttcgacaac aatacaacag cttctt                                36

<210> SEQ ID NO 17
<211> LENGTH: 65
<212> TYPE: DNA
<213> ORGANISM: Artificial Sequence
<220> FEATURE:
<223> OTHER INFORMATION: sequence extended from the detection probe (5'
      part)

<400> SEQUENCE: 17
gaucgcauuu ggacuucugc cttttttggg acttttcttc ttcgacaaca atacaacagc      60
ttctt                                                                  65
```

METHOD FOR DETECTING TARGET MOLECULE IN WHICH ROLLING CIRCLE AMPLIFICATION IS USED

A Sequence Listing, which is a part of the present disclosure, is submitted concurrently with the specification as a text file. The name of the text file containing the Sequence Listing is "54697 SubSeqlisting.txt." The Substitute Sequence Listing was created on Jan. 24, 2022, and is an ASCII text file which is 3,940 bytes in size. The subject matter of the Substitute Sequence Listing is incorporated herein in its entirety by reference.

TECHNICAL FIELD

The present invention relates to a method of detecting a target molecule using a rolling circle amplification method.

BACKGROUND ART

Recent interest has focused on development of detection methods for diseases and stresses using, as targets, nucleic acid mutations and biologically relevant molecules such as biomarkers. The real-time PCR method and the like are known as nucleic acid mutation detection methods, and the ELISA method and the like are known as detection methods for biomolecules such as proteins and metabolites. However, requirement of expensive devices and high usage costs, and also complicated operation, prevents use of these methods for simple tests at clinics or for self-medication.

A method in which RNA is detected by the rolling circle amplification method has been disclosed in Patent Document 1. However, this method enables only detection of the sequence at the 3'-end since the method uses the analyte RNA as a primer. This method is insufficient also from the viewpoint of the amplification efficiency and the detection efficiency.

Patent Document 2 and Non-patent Document 1 disclose detection methods for polynucleotides using a single-stranded circular DNA, a primer, and a guanine quadruplex-binding reagent. However, they do not disclose application to detection methods for non-nucleic acid molecules such as proteins.

PRIOR ART DOCUMENTS

Patent Documents

[Patent Document 1] JP 2012-080871 A
[Patent Document 2] WO 2016/152936

Non-Patent Document

[Non-patent Document 1] Anal. Chem., 2016, 88 (14), pp 7137-7144

SUMMARY OF THE INVENTION

An object of the present invention is to provide a simple method for efficiently detecting a target molecule such as a protein.

In order to solve the above problems, the present inventors intensively studied. As a result, the present inventors discovered that a non-nucleic acid molecule can be efficiently detected by a rolling circle amplification method using a single-stranded circular DNA, a capture DNA, and a primer, wherein the sequences of the capture DNA and the primer are aptamer sequences that bind to the target non-nucleic acid molecule, thereby completing the present invention.

According to a first embodiment of the present invention, a method of detecting a target molecule, the method comprising the steps of:

forming a complex of a target molecule, a capture oligonucleotide, an oligonucleotide primer, and a single-stranded circular DNA;

performing a nucleic acid amplification reaction by rolling circle amplification based on the formation of the complex; and detecting amplified nucleic acid;

wherein the single-stranded circular DNA contains a first region, and a second region linked to the 3'-side of the first region;

the oligonucleotide primer contains a first aptamer sequence which binds to the target molecule, and a sequence which is linked to the 3'-side of the first aptamer sequence and is complementary to the first region of the single-stranded circular DNA; and the capture oligonucleotide contains a sequence complementary to the second region of the single-stranded circular DNA, and a second aptamer sequence which is linked to the 3'-side of the sequence complementary to the second region and binds to the target molecule;

is provided.

According to a second embodiment of the present invention, a method of detecting a target molecule, the method comprising the steps of:

forming a first complex containing a target molecule, a capture oligonucleotide, a first oligonucleotide primer, and a first single-stranded circular DNA;

performing a nucleic acid amplification reaction by rolling circle amplification based on the formation of the first complex;

hybridizing a second single-stranded circular DNA and a second oligonucleotide primer with an elongated chain generated by the nucleic acid amplification reaction, to form a second complex containing the elongated chain, the second oligonucleotide primer, and the second single-stranded circular DNA;

performing a nucleic acid amplification reaction by rolling circle amplification based on the formation of the second complex; and detecting amplified nucleic acid;

wherein the first single-stranded circular DNA contains a first region, a second region linked to the 3'-side of the first region, and a sequence complementary to a second-single-stranded-circular-DNA-binding sequence;

the first primer contains a first aptamer sequence which binds to the target molecule, and a sequence which is linked to the 3'-side of the first aptamer sequence and is complementary to the first region of the first single-stranded circular DNA;

the capture oligonucleotide contains a sequence complementary to the second region of the first single-stranded circular DNA, and a second aptamer sequence which is linked to the 3'-side of the sequence complementary to the second region and binds to the target molecule;

the second single-stranded circular DNA contains the sequence identical to the sequence complementary to the second-single-stranded-circular-DNA-binding sequence in the first single-stranded circular DNA, a second oligonucleotide primer-binding sequence adjacent to the 5'-side of said sequence, and a sequence complementary to a detection reagent-binding sequence; and the second oligonucleotide primer contains the sequence identical to a region adjacent to the 5'-side of the sequence complementary to the second-single-stranded-circular-DNA-binding sequence in the first single-stranded circular DNA, and a sequence which is adjacent to the 3'-side of said sequence and is complementary to the second oligonucleotide primer-binding sequence in the second single-stranded circular DNA;

is provided.

The detection reagent-binding sequence is preferably a guanine quadruplex-forming sequence, and the detection reagent is preferably a guanine quadruplex-binding reagent. The guanine quadruplex-binding reagent is preferably the later-mentioned ThT derivative.

According to the present invention, in the presence of a target molecule, a complex is formed by a capture oligonucleotide, an oligonucleotide primer, and a single-stranded circular DNA, and then nucleic acid amplification reaction occurs therefrom to generate a DNA chain containing a number of detection reagent-binding sequences such as guanine quadruplex-containing sequences linearly bound to each other. By detecting the resulting DNA chain using a detection reagent such as ThT (derivative), the target molecule can be specifically detected. Since the present invention uses the RCA method, in which the reaction proceeds at a constant temperature, rather than the PCR method, which requires a temperature cycle of, for example, increasing/decreasing the temperature, the present invention can be applied to simple detection methods. The method of the present invention is useful for uses such as examinations and diagnoses.

EMBODIMENTS FOR CARRYING OUT THE INVENTION

<Target Molecule>

Figure 1:
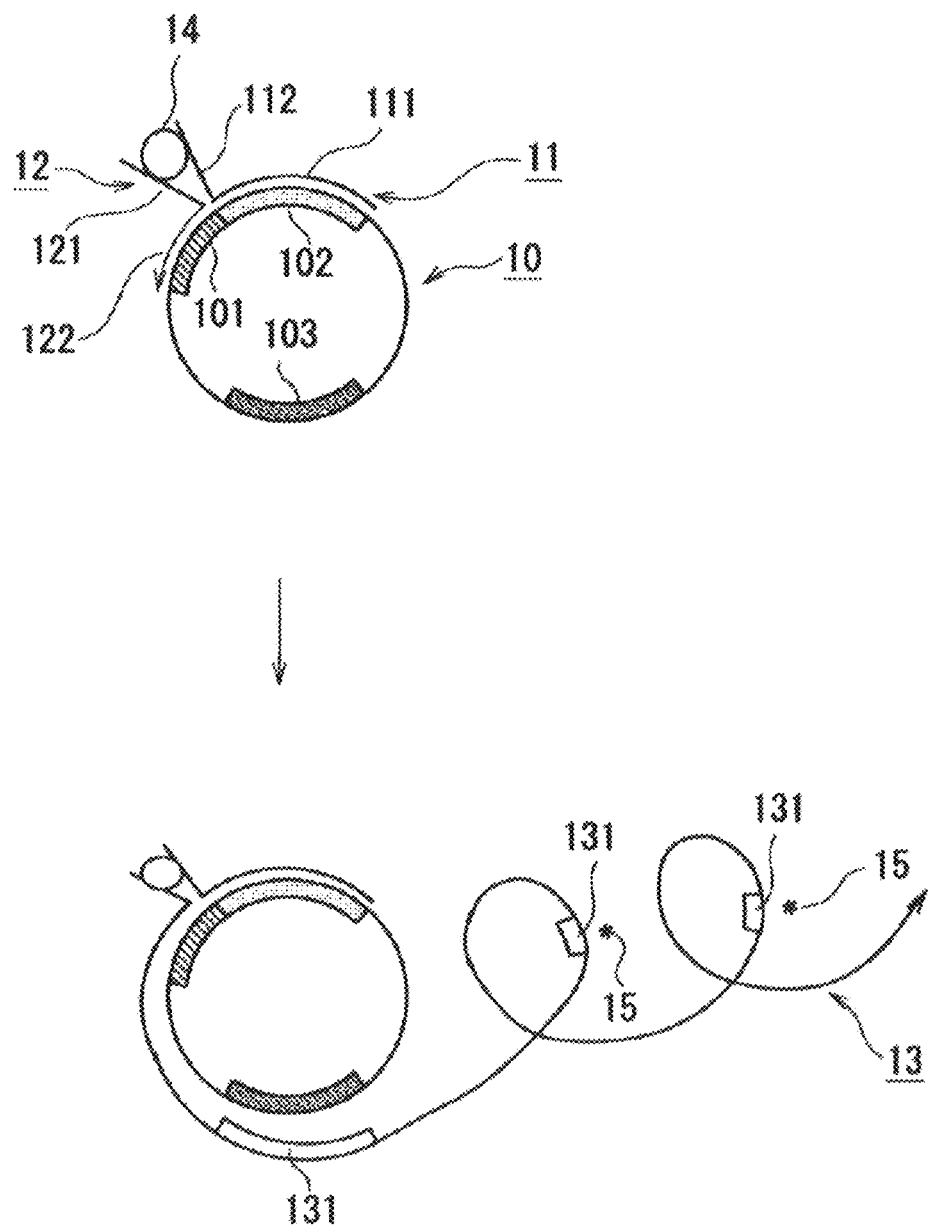
FIG. 1 is a schematic diagram illustrating a target molecule detection method according to a first embodiment of the present invention.

In the present description, the target molecule is not limited as long as it is a molecule capable of binding to the first aptamer sequence and the second aptamer sequence. The target molecule is preferably a non-nucleic acid molecule, and examples of the molecule include proteins, peptides, and low molecular weight compounds, and also include sugars, vitamins, hormones, and coenzymes.

Examples of the hormones include adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone-releasing hormone, human chorionic gonadotropin, histamine, human placental lactogen, insulin, insulin-like growth factor, growth hormone, inhibin, leptin, leukotriene, lipotropin, melatonin, orexin, oxytocin, parathyroid hormone, progesterone, prolactin, prolactin-releasing hormone, prostaglandin, renin, serotonin, secretin, somatostatin, thrombopoietin, thyroid-stimulating hormone, thyrotropin-releasing hormone, thyroxine, triiodothyronine, and vasopressin.

Examples of the proteins include blood coagulation factors such as thrombin; virus-derived proteins; cytokines and growth factors (which may correspond to the above-described hormones); and disease marker proteins such as tumor markers.

The target molecule may be an isolated molecule, or a molecule contained in a sample derived from an organism species. Examples of such a sample containing a target molecule include samples containing a virus, prokaryote, or eukaryote. In cases of vertebrates (including human), examples of the sample include excrements such as feces, urine, and sweat; and body fluids such as blood, semen, saliva, gastric juice, and bile. The sample may also be a tissue surgically removed from a body, or a tissue dropped from a body such as a body hair. The sample may also be a sample prepared from a processed product of food or the like.

Detection Method: First Embodiment

The method of detecting a target molecule according to the first embodiment of the present invention is a method of detecting a target molecule, the method comprising the steps of:

forming a complex of a target molecule, a capture oligonucleotide, an oligonucleotide primer, and a single-stranded circular DNA;

performing a nucleic acid amplification reaction by rolling circle amplification based on the formation of the complex; and detecting amplified nucleic acid.

The first embodiment is described below.

<Single-Stranded Circular DNA>

The single-stranded circular DNA contains: a first region, and a second region linked to the 3'-side of the first region; and preferably further contains a sequence complementary to a detection reagent-binding sequence such as a guanine quadruplex-forming sequence.

A description is given below showing an example with reference to FIG. 1. The single-stranded circular DNA is illustrated in the 5'→3' clockwise direction. A single-stranded circular DNA 10 contains: a first region 101 (primer-binding sequence), a second region 102 (sequence complementary to a first region 111 of a capture oligopolynucleotide 11) linked to the 3'-side of the first region 101, and a sequence 103 complementary to a guanine quadruplex-forming sequence. The sequence 101 has a length of preferably 7 bases or 8 bases. The sequence is not limited, and has a GC content of preferably 30 to 70%. The sequence 102 has a length of usually 10 to 30 bases, preferably 15 to 25 bases, and a GC content of preferably 30 to 70%.

Examples of the guanine quadruplex-forming sequence include a sequence described in Nat Rev Drug Discov. 2011 April; 10(4): 261-275, and can be represented as $G_3N_{1-10}G_3N_{1-10}G_3N_{1-10}G_3$. Specific examples of the sequence include the sequences of SEQ ID NOs:1 to 6. Examples of the sequence complementary to the guanine quadruplex-forming sequence include $C_3N_{1-10}C_3N_{1-10}C_3N_{1-10}C_3$. That is, in the sequence, three consecutive C's are repeated four times via spacers each having a sequence composed of one to ten (preferably one to five) arbitrary bases (N=A, T, G, or C).

```
22 mer DNAs
(22AG: 5'-AGGGTTAGGGTTAGGGTTAGGG-3' (SEQ ID

NO: 1) and 22Kit: 5'-AGGGAGGGCGCTGGGAGGAGG

G-3' (SEQ ID NO: 2)), 26 mer DNA
(26Tel: 5'-TTAGGGTTAGGGTTAGGGTTAGGGTT-3'

(SEQ ID NO: 3)), 27 mer DNA (27Myc: 5'-TGGGGAGGGTGGGGAGGGT

GGGGA AGG-3' (SEQ ID NO: 4)), 20 mer DNA
(20Src: 5'-GGGCGGCGGGCTGGGCGGGG-3'

(SEQ ID NO: 5)), 18 mer RNA (18Ras: 5'-GGGAGGGGCGGGUCUG

GG-3' (SEQ ID NO: 6)).
```

The sequence complementary to the guanine quadruplex-forming sequence may have arbitrary sequences before and after it, that is, between it and the first region 101, and between it and the second region 102. The total length of the single-stranded circular DNA 10 is preferably 35 to 100 bases.

Although FIG. 1 describes a case where the detection reagent-binding sequence is a guanine quadruplex-forming sequence, the detection may also be carried out, for example, using an aptamer sequence or a molecular beacon (hairpin-shaped oligonucleotide having a fluorescent group (donor) and a quenching group (acceptor) that cause FRET)-binding sequence as the detection reagent-binding sequence, and using an aptamer-binding coloring molecule or a molecular beacon as the detection reagent. The detection may also be carried out using a labeled probe that hybridizes with the detection reagent-binding sequence.

The single-stranded circular DNA 10 can be obtained by circularization of a single-stranded DNA (ssDNA). The circularization of the single-stranded DNA can be carried out by arbitrary means. It can be carried out by using, for example, CircLigase™ (Lucigen), CircLigase™ (Lucigen), ssDNA Ligase (Epicentre), or ThermoPhage™ single-stranded DNA ligase (Prokzyme).

<Oligonucleotide Primer>

The oligonucleotide primer contains a first aptamer sequence which binds to a target molecule, and a sequence which is linked to the 3'-side of the first aptamer sequence and is complementary to the first region of the single-stranded circular DNA. The sequence of the oligonucleotide primer may be a DNA sequence, an RNA sequence, or a mixed sequence of DNA and RNA. As long as the aptamer-binding properties, the hybridization properties, and the extension properties are retained, the sequence may be a sequence further containing a modified nucleic acid or a nucleic acid analog.

In FIG. 1, the oligonucleotide primer 12 contains a first aptamer sequence 121 which binds to the target molecule 14, and a sequence 122 which is linked to the 3'-side of the first aptamer sequence 121 and is complementary to the first region 101 of the single-stranded circular DNA. The first aptamer sequence 121 has a length of usually 10 to 30 bases, preferably 15 to 25 bases, and a GC content of preferably 30 to 70%. The sequence 122 which is complementary to the first region 101 of the single-stranded circular DNA has a length of preferably 7 to 8 bases.

The primer may be provided as an immobilized primer by, for example, immobilization on a carrier. By this, detection on the solid phase becomes possible. Examples of the method of the immobilization include a method in which the primer is labeled with biotin or the like, and then immobilized by interaction with avidin or the like.

The aptamer sequence is a sequence that binds to the target molecule described above. The aptamer may be a sequence known as an aptamer sequence of the target molecule (for example, a sequence described in the aptamer database described in Nucleic Acids Res (2004) 32 (suppl_1): D95-D100.), or may be a sequence selected using SELEX (Stoltenburg, R. et al. (2007), Biomolecular Engineering 24, pp. 381-403; Tuerk, C. et al., Science 249, pp. 505 to 510; Bock, L. C. et al. (1992), Nature 355, pp. 564-566) or non-SELEX (Berezovski, M. et al. (2006), Journal of the American Chemical Society 128, pp. 1410-1411).

Two kinds of aptamer sequences that bind to the target molecule may be used as the first and second aptamer sequences.

As the first and second aptamer sequences, the two kinds of sequences may be separately selected. Alternatively, a split aptamer obtained by cleavage of an aptamer sequence which forms a stem-loop structure or a bulge-loop structure and binds to the target molecule at two sites, which cleavage is carried out at a loop portion, may be used as the first and second aptamers.

<Capture Oligonucleotide>

The capture oligonucleotide contains a sequence complementary to the second region of the single-stranded circular DNA, and a second aptamer sequence which is linked to the 3'-side thereof and which binds to the target molecule. The sequence of the capture oligonucleotide may be a DNA sequence, an RNA sequence, or a mixed sequence of DNA and RNA. As long as the hybridization properties and the aptamer-binding properties are retained, the sequence may be a sequence further containing a modified nucleic acid or a nucleic acid analog.

As illustrated in FIG. 1, the capture oligonucleotide 11 contains a sequence 111 complementary to the second region 102 of the single-stranded circular DNA 10, and a second aptamer sequence 112 which is linked to the 3'-side of the sequence 111 and binds to the target protein.

Each of the sequence 111 and the sequence 112 has a length of usually 10 to 30 bases, preferably 15 to 25 bases, and a GC content of preferably 30 to 70%.

For preventing occurrence of non-specific extension reaction from the second aptamer sequence 112, the 3'-end of the second aptamer sequence 112 is preferably modified with a phosphate group or the like.

<Amplification Method>

In the presence of the target molecule 14, a quaternary complex of the target molecule 14, the capture oligonucleotide 11, the single-stranded circular DNA 10, and the oligonucleotide primer 12 is formed, and, as a result, nucleic acid amplification reaction by the rolling circle amplification (RCA) method occurs.

Conditions for the formation of the quaternary complex may be appropriately set taking into account the combination of the target molecule, the single-stranded circular DNA, the capture oligonucleotide, and the oligonucleotide primer.

However, since aptamers are used at detection portions, it is desirable to use a reaction liquid containing a monovalent alkali metal ion(s) and/or a divalent alkaline earth metal ion(s), and the salt concentration for one or more of these may be appropriately set. However, since reaction of rolling circle amplification (RCA) is inhibited at high salt concentration, the salt concentration of the metal ion(s) is preferably 0 to 20 mM.

The RCA method is described in, for example, Lizardi et al., Nature Genet. 19: 225-232 (1998); U.S. Pat. Nos. 5,854,033 B; 6,143,495 B; and WO 97/19193. The RCA method can be carried out using, for example, a mesophilic chain-substituting DNA synthetase such as phi29 polymerase, Klenow DNA Polymerase (5'-3', 3'-5' exo minus), Sequenase™ Version 2.0 T7 DNA Polymerase (USB®), Bsu DNA Polymerase, Large Fragment (NEB); or a heat-resistant chain-substituting DNA synthetase such as Bst DNA Polymerase (Large Fragment) (NEB), Bsm DNA Polymerase, Large Fragment (Fermentas), BcaBEST™ DNA polymerase (TakaraBio), Vent® DNA polymerase (NEB), Deep Vent® DNA polymerase (NEB), or DisplaceAce™ DNA Polymerase (Epicentre).

The extension reaction of DNA by RCA does not require use of a thermal cycler, and is carried out, for example, at a constant temperature within the range of 25° C. to 65° C. The reaction temperature is appropriately set according to an ordinary procedure based on the optimum temperature of the enzyme and the denaturation temperature (the temperature range in which binding (annealing) of the primer to, or dissociation of the primer from, the template DNA occurs), which is dependent on the primer chain length. The reaction may also be carried out at a constant, relatively low temperature. For example, in cases where phi29DNA polymerase is used as the chain-substituting DNA synthetase, the reaction is carried out preferably at 25° C. to 42° C., more preferably at about 30 to 37° C. By the RCA, nucleic acid (amplification product 13) containing a guanine quadruplex-forming sequence (corresponding to the sequence 103) is amplified dependently on the target molecule 14 from the primer 12 along the single-stranded circular DNA 10. Since the amplification product 13 contains a sequence 131 containing a guanine quadruplex, it can be detected with a guanine quadruplex detection reagent 15. Accordingly, the detection method of the present invention enables detection and quantification of the target molecule.

Detection Method: Second Embodiment

The detection method according to the second embodiment of the present invention comprises the steps of:

forming a first complex containing a target molecule, a capture oligonucleotide, a first oligonucleotide primer, and a first single-stranded circular DNA;

performing a nucleic acid amplification reaction by rolling circle amplification based on the formation of the first complex;

hybridizing a second single-stranded circular DNA and a second oligonucleotide primer with an elongated chain generated by the nucleic acid amplification reaction, to form a second complex containing the elongated chain, the second oligonucleotide primer, and the second single-stranded circular DNA;

performing a nucleic acid amplification reaction by rolling circle amplification based on the formation of the second complex; and detecting amplified nucleic acid.

The second embodiment is described below.

The capture oligonucleotide and the first oligonucleotide primer in the second embodiment are the same as those described for the first embodiment.

<First Single-Stranded Circular DNA>

The first single-stranded circular DNA contains: a first region, a second region linked to the 3'-side thereof, and a sequence complementary to a second-single-stranded-circular-DNA-binding sequence.

A description is given below with reference to FIG. 2.

A first single-stranded circular DNA 20 contains: a first region 201 (primer-binding sequence), a second region 202 (sequence complementary to a first region 211 of a capture oligonucleotide 21), and a sequence 203 complementary to a second-single-stranded-circular-DNA-binding sequence.

The first region 201 has a length of preferably 7 bases or 8 bases. Its sequence is not limited, and has a GC content of preferably 30 to 70%. The second region 202 has a length of usually 10 to 30 bases, preferably 15 to 25 bases, and a GC content of preferably 30 to 70%. The sequence 203 complementary to a second-single-stranded-circular-DNA-binding sequence has a length of usually 10 to 30 bases, preferably 15 to 25 bases, and a GC content of preferably 30 to 70%. The total length of the first single-stranded circular DNA 20 is preferably 35 to 100 bases. The first single-stranded circular DNA 20 can be obtained by circularization of a single-stranded DNA (ssDNA) by the method described above.

<Second Single-Stranded Circular DNA>

A second single-stranded circular DNA 24 contains:

the sequence 241 identical to the sequence 203 complementary to the second-single-stranded-circular-DNA-binding sequence in the first single-stranded circular DNA 20;

a second primer-binding sequence 242 adjacent to the 5'-side of the sequence 241; and a sequence 243 complementary to a guanine quadruplex-forming sequence.

The sequence 203 has a length of usually 10 to 30 bases, preferably 15 to 25 bases, and a GC content of preferably 30 to 70%. The sequence 242 has a length of 7 bases or 8 bases. The sequence is not limited, and has a GC content of preferably 30 to 70%. The sequence 243 complementary to a guanine quadruplex-forming sequence is the same as that described for the first embodiment. The total length of the second single-stranded circular DNA 24 is preferably 35 to 100 bases. The second single-stranded circular DNA 24 can be obtained by circularization of a single-stranded DNA (ssDNA) by the method described above.

Figure 2:
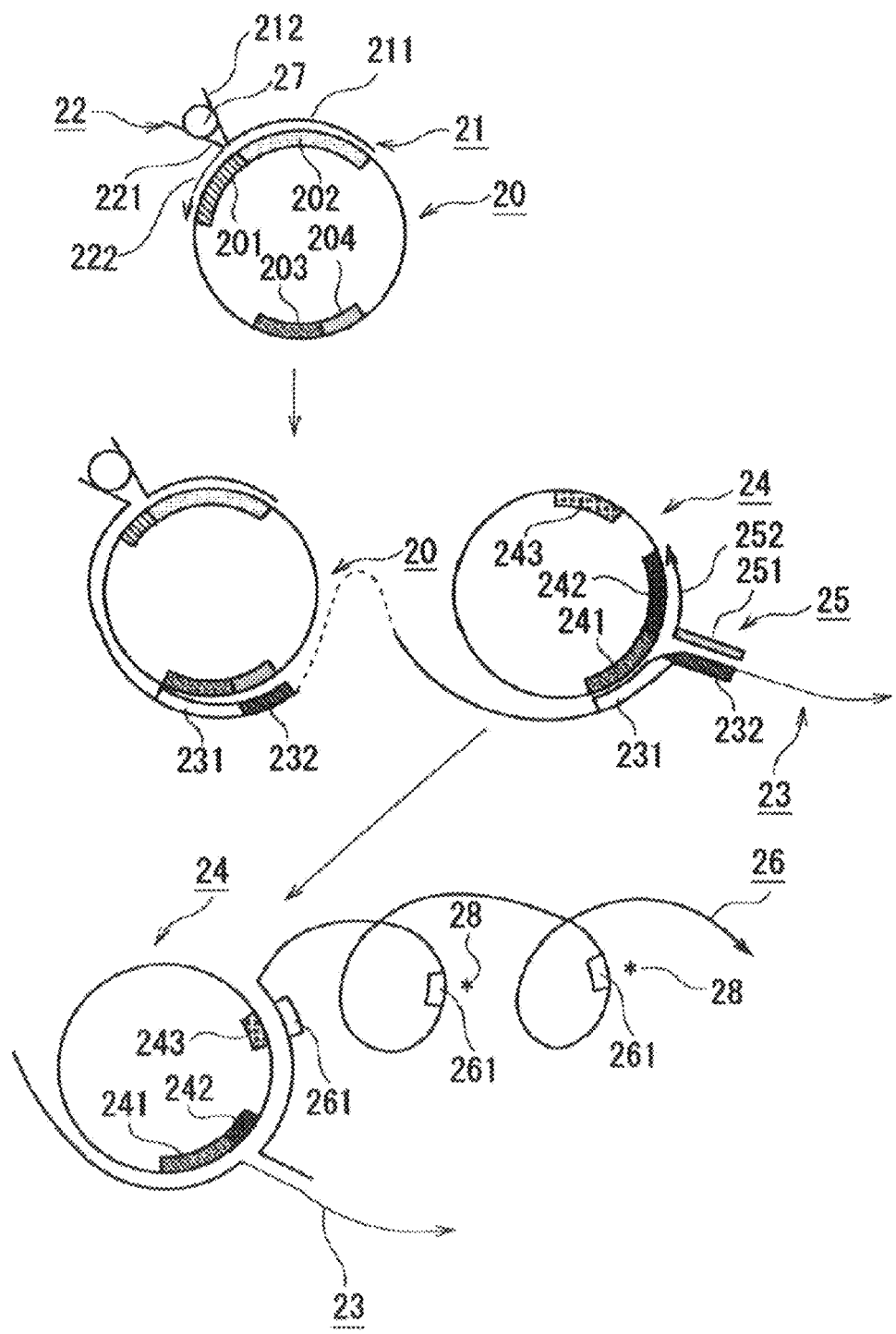
FIG. 2 is a schematic diagram illustrating a target molecule detection method according to a second embodiment of the present invention.

Although FIG. 2 describes a case where the detection reagent-binding sequence is a guanine quadruplex-forming sequence, the detection may also be carried out using an aptamer sequence or a molecular beacon (hairpin-shaped oligonucleotide having a fluorescent group (donor) and a quenching group (acceptor) that cause FRET)-binding sequence as the detection reagent-binding sequence, and using an aptamer-binding coloring molecule or a molecular beacon as the detection reagent (ChemBioChem 2007, 8, 1795-1803; J. Am. Chem. Soc. 2013, 135, 7430-7433).

<Second Oligonucleotide Primer>

A second oligonucleotide primer 25 contains: the sequence 251 (preferably a sequence of 8 to 15 bases) identical to the region 204 adjacent to the 5'-side of the sequence 203 complementary to the second-single-stranded-circular-DNA-binding sequence in the first single-stranded circular DNA 20; and a sequence 252 (preferably a sequence of 7 to 8 bases) adjacent to the 3'-side of the sequence 251 and complementary to the second primer-binding sequence 242 of the second single-stranded circular DNA. The sequence of the second oligonucleotide primer may be a DNA sequence, an RNA sequence, or a mixed sequence of DNA and RNA. As long as the hybridization properties and the extension properties are retained, the sequence may be a sequence further containing a modified nucleic acid or a nucleic acid analog.

<Amplification Method>

As shown in FIG. 2, in the presence of a target molecule 27, a quaternary complex of the target molecule 27, the capture oligonucleotide 21, the single-stranded circular DNA 20, and the primer 22 is formed, and, as a result, nucleic acid amplification reaction by the rolling circle amplification (RCA) method occurs. The reaction conditions and the like are the same as those for the first embodiment. By the RCA, a first amplification product 23 is amplified dependently on the target molecule 27 from the primer 22 along the first single-stranded circular DNA 20.

The amplification product 23 contains a sequence 231 complementary to the sequence 203, in the first single-stranded circular DNA 20, complementary to the second-single-stranded-circular-DNA-binding sequence. Therefore, the second single-stranded circular DNA 24, which contains the sequence 241 identical to the sequence 203, hybridizes with the sequence 231 of the first amplification product 23 via the sequence 241.

With the thus formed complex of the first amplification product 23 and the second single-stranded circular DNA, the second oligonucleotide primer 25 hybridizes to form a ternary complex.

That is, since the second oligonucleotide primer 25 contains the sequence 251 identical to the region 204, in the first single-stranded circular DNA 20, adjacent to the 5'-side of the sequence 203 complementary to the second-single-stranded-circular-DNA-binding sequence, the second oligonucleotide primer 25 hybridizes with the region 232 of the first amplification product 23, which region is complementary to the region 204 of the first single-stranded circular DNA 20, via the sequence 251.

Since the second oligonucleotide primer 25 contains, in the 3'-side of the sequence 251, the sequence 252 complementary to the second primer-binding sequence 242 of the second single-stranded circular DNA 24, the second oligonucleotide primer 25 also hybridizes with the second single-stranded circular DNA 24 via the sequence 252.

By RCA, a second amplification product 26 (elongated chain) is amplified from the resulting ternary complex of the first amplification product 23, the second single-stranded circular DNA 24, and the second oligonucleotide primer 25. Since the second amplification product 26 contains a sequence 261 containing a guanine quadruplex, it can be detected with a guanine quadruplex detection reagent 28. In the second embodiment, the second single-stranded circular DNA 24 hybridizes with each region 231 contained in the first amplification product 23 to cause the RCA reaction. Thus, a remarkable improvement in the detection sensitivity can be achieved.

In the presence of a target molecule, a quaternary complex of the target molecule, the capture oligonucleotide, the single-stranded circular DNA, and the oligonucleotide primer is formed, and, as a result, amplification reaction occurs to allow detection of the amplification product. On the other hand, in the absence of the target molecule, the amplification reaction does not occur, so that the amplification product is not detected. Accordingly, the detection method of the present invention enables detection and quantification of the target molecule.

<Detection Reagent>

As described above, the combination of the detection reagent-binding sequence and the detection reagent may be arbitrarily decided, and examples of the combination include combinations of an aptamer sequence and an aptamer-binding coloring molecule, combinations of a molecular beacon-binding molecule and a molecular beacon, and combinations of a specific sequence and a labeled probe that hybridizes therewith. The combination is preferably a combination of a guanine quadruplex and a guanine quadruplex-binding reagent. Examples of the guanine quadruplex-binding reagent include the following reagents.

[1] Thioflavin T (ThT) or a derivative thereof

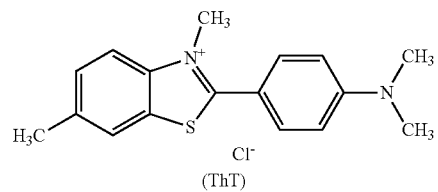

(ThT)

[2] H-aggregate "Yan, J. W.; Ye, W. J.; Chen, S. B.; Wu, W. B.; Hou, J. Q.; Ou, T. M.; Tan, J. H.; Li, D.; Gu, L. Q.; Huang, Z. S. Anal. Chem. 2012, 84, 6288-6292."

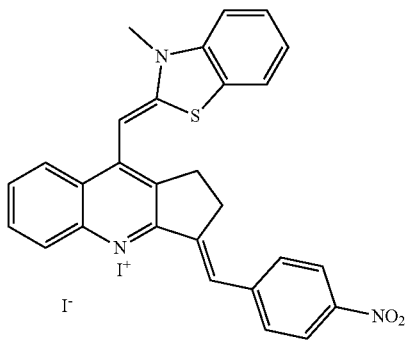

[3] TMPyP4 "Yaku, H.; Fujimoto, T.; Murashima, T.; Miyoshi, D.; Sugimoto, N. Chem. Commun. 2012, 48, 6203-6216."

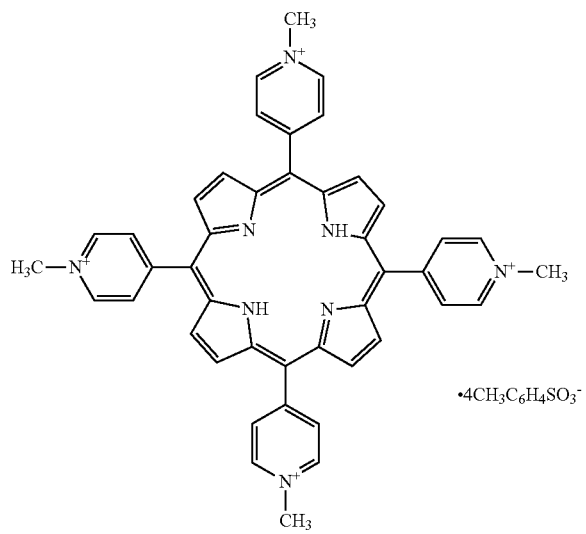

[4] PPIX "Li, T.; Wang, E.; Dong, S. Anal. Chem. 2010, 82, 7576-7580."

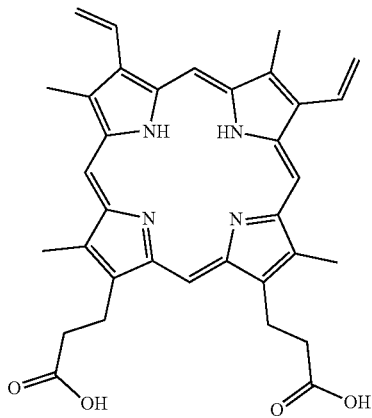 [SMILES: C=Cc1c(C)c2cc3[nH]c(cc4nc(cc5nc(cc1[nH]2)C(C)=C5CCC(=O)O)C(CCC(=O)O)=C4C)c(C)c3C=C]

[5] BPBC "Jin, B.; Zhang, X.; Zheng, W.; Liu, X.; Qi, C.; Wang, F.; Shangguan, D. Anal. Chem. 2014, 86, 943-952."
[6] APD "Nikan, M.; Di Antonio, M.; Abecassis, K.; McLuckie, K.; Balasubramanian, S. Angew. Chem., Int. Ed. 2013, 52, 1428-1431."

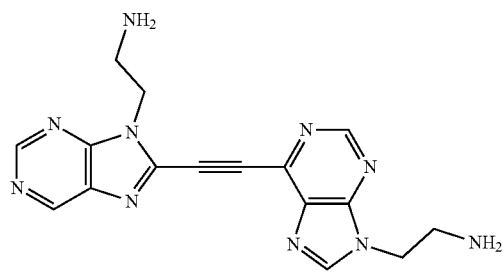 [SMILES: NCCn1cnc2c(C#Cc3nc4cncnc4n3CCN)ncnc21]

[7] Thiazole Orange (TO) "Nakayama S.; Kelsey I.; Wang J.; Roelofs K.; Stefane B.; Luo Y.; Lee V.T.; Sintim H. O. J. Am. Chem. Soc. 2011, 133, 4856-4864."

Preferably, a ThT derivative represented by the following General Formula (I) may be used (Anal. Chem. 2014, 86, 12078-12084). JP 2016-079132 A.

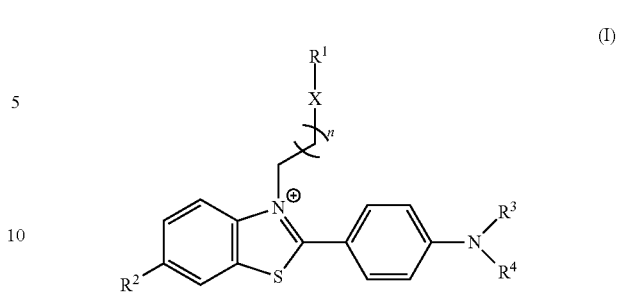

In this formula, $R^1$ represents hydrogen, or a $C_1$-$C_{10}$ (preferably $C_1$-$C_5$) hydrocarbon group which optionally contains one or more selected from the group consisting of O, S, and N. The hydrocarbon group may be either linear or branched, or either saturated or unsaturated. The hydrocarbon group may be an aliphatic hydrocarbon group such as an alkyl group, or may be an aromatic hydrocarbon group such as an aryl group or an arylalkyl group. The term "optionally contains one or more selected from the group consisting of O, S, and N" means that the hydrocarbon group may contain a functional group containing a nitrogen atom, oxygen atom, sulfur atom, or the like, such as an amino group (—NR$_2$) (wherein each R independently represents hydrogen or a $C_1$-$C_5$ alkyl group), nitro group (—NO$_2$), cyano group (—CN), isocyanate group (—NCO), hydroxyl group (—OH), aldehyde group (—CHO), carboxyl group (—COOH), mercapto group (—SH), or sulfonic acid group (—SO$_3$H), or that a linking group containing a nitrogen atom, oxygen atom, sulfur atom, or the like, such as an ether group (—O—), imino group (—NH—), thioether group (—S—), carbonyl group (—C(=O)—), amide group (—C(=O)—NH—), ester group (—C(=O)—O—), or thioester group (—C(=O)—S—), may be contained in the inside or at a terminus of the carbon backbone of the hydrocarbon group.

$R^2$, $R^3$, and $R^4$ each independently represent a $C_1$-$C_5$ (aliphatic) hydrocarbon group, more preferably a $C_1$-$C_3$ hydrocarbon group, especially preferably a methyl group. The $C_1$-$C_5$ hydrocarbon group may be either linear or branched, or either saturated or unsaturated.

n represents an integer of 0 to 5, more preferably an integer of 0 to 3, especially preferably 1.

X represents O, S, or NH, more preferably O.

Specific examples of the compound include the following.

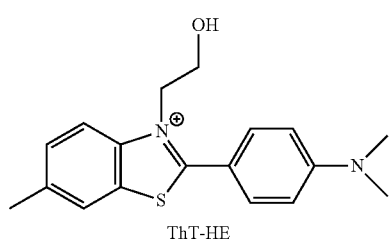

ThT-HE

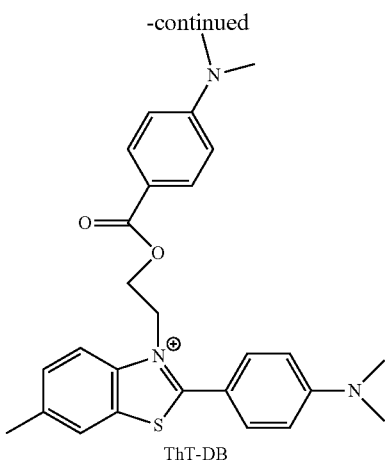

ThT-DB

The detection of the guanine quadruplex structure in the test DNA can be carried out by, for example, bringing a compound represented by General Formula (I) or a salt thereof into contact with a sample containing the RCA product, and detecting the compound bound to the guanine quadruplex structure based on fluorescence emitted from the compound. The detection operation itself is the same as a known method except that the compound represented by General Formula (I) or a salt thereof is used. The detection operation can be carried out by bringing a solution prepared by dissolving the compound in a buffer into contact with a sample containing a test DNA, incubating the resulting mixture, carrying out washing, and then detecting fluorescence from the fluorescent dye bound to the test DNA after the washing.

The target molecule detection reagent in the present invention comprises:

a single-stranded circular DNA containing a first region, and a second region linked to the 3'-side thereof;

an oligonucleotide primer containing a first aptamer sequence which binds to a target molecule, and a sequence which is linked to the 3'-side thereof and which is complementary to the first region of the single-stranded circular DNA; and a capture oligonucleotide containing a sequence complementary to the second region of the single-stranded circular DNA, and a second aptamer sequence which is linked to the 3'-side thereof and which binds to the target molecule;

which are as described above.

The single-stranded circular DNA may further contain a sequence complementary to a detection reagent-binding sequence such as a guanine quadruplex-forming sequence.

The target molecule detection reagent in the present invention may further contain the second single-stranded circular DNA and the second oligonucleotide primer, and further, a detection reagent such as a guanine quadruplex-binding reagent.

EXAMPLES

The present invention is described below by way of Examples. However, the present invention is not limited to the embodiments of the following Examples.

Example 1-1

Figure 4:
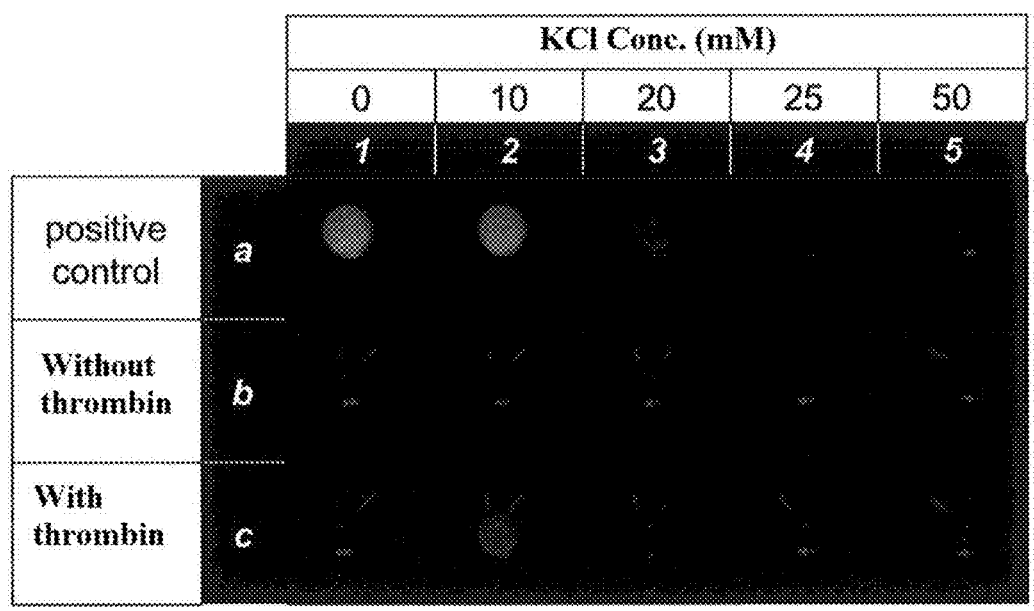
FIG. 4 is a diagram (photographs) illustrating results of detection of thrombin in Example 1-1.

Thrombin Detection Method Using Split Aptamer
Preparation of a1 to a5 of FIG. 4

A mixture was prepared with 2 µL of 100 nM DNA template [2] (final concentration, 10 nM), 2 µL of 400 nM DNA template [1] (final concentration, 40 nM), 2 µL of 120 nM Positive control Primer (final concentration, 12 nM), 2 µL of 480 nM DNA primer [1] (final concentration, 48 nM), 2 µL of 10×attached buffer, 1 µL of 20×attached BSA solution, 2 µL of 10 mM dNTPs (final concentration, 1 mM), 1 µL of 0 to 1000 mM KCl solution (final concentration, 0 to 50 mM), 2 µL of 1 U/µL Phi29 Polymerase (final concentration, 0.1 U/µL), and 4 µL of water (20 µL in total).

Preparation of a1 to b5 of FIG. 4

A mixture was prepared with 2 µL of 100 nM DNA template [2] (final concentration, 10 nM), 2 µL of 400 nM DNA template [1] (final concentration, 40 nM), 2 µL of 120 nM Capture Probe [1] (final concentration, 12 nM), 2 µL of 120 nM Detection Probe [1] (final concentration, 12 nM), 2 µL of 480 nM DNA primer [1] (final concentration, 48 nM), 2 µL of 10×attached buffer, 1 µL of 20×attached BSA solution, 2 µL of 10 mM dNTPs (final concentration, 1 mM), 1 µL of 0 to 1000 mM KCl solution (final concentration, 0 to 50 mM), 2 µL of 1 U/µL Phi29 Polymerase (final concentration, 0.1 U/µL), and 2 µL of water (20 µL in total).

Preparation of c1 to c5 of FIG. 4

A mixture was prepared with 2 µL of 100 nM DNA template [2] (final concentration, 10 nM), 2 µL of 400 nM DNA template [1] (final concentration, 40 nM), 2 µL of 120 nM Capture Probe [1] (final concentration, 12 nM), 2 µL of 120 nM Detection Probe [1] (final concentration, 12 nM), 2 µL of 480 nM DNA primer [1] (final concentration, 48 nM), 2 µL of 10×attached buffer, 1 µL of 20×attached BSA solution, 2 µL of 10 mM dNTPs (final concentration, 1 mM), 1 µL of 0 to 1000 mM KCl solution (final concentration, 0 to 50 mM), 2 µL of 1 U/µL Phi29 Polymerase (final concentration, 0.1 U/µL), and 2 µL of 1 µM thrombin solution (final concentration, 100 nM) (20 µL in total).

Example 1-2

Figure 5:
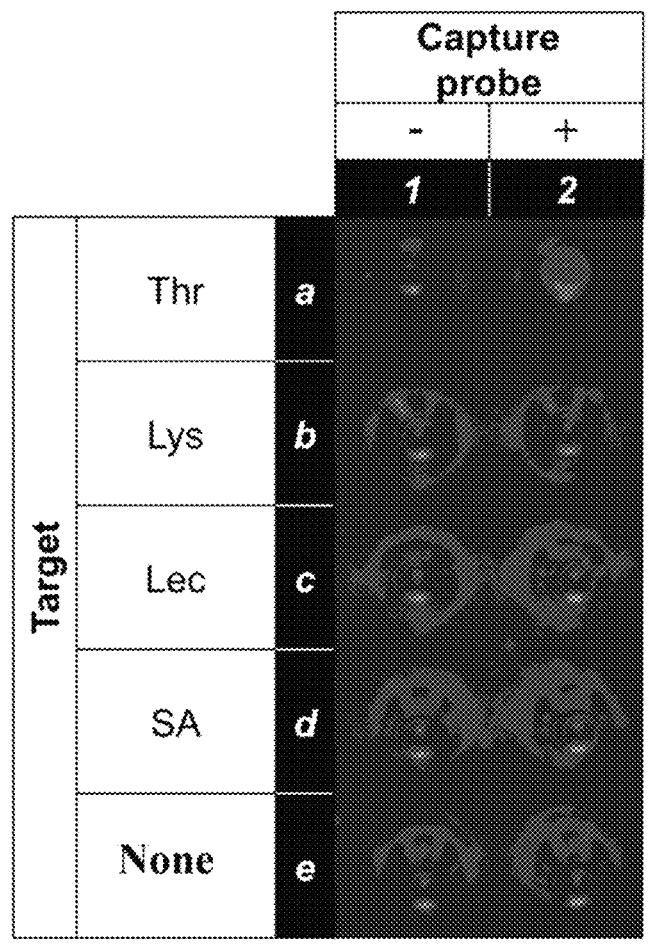
FIG. 5 is a diagram (photographs) illustrating results of detection of thrombin in Example 1-2.

Thrombin Detection Method Using Split Aptamer (Confirmation of Absence of Reaction with Other Molecules)
Preparation of a1 and a2 of FIG. 5

A mixture was prepared with 2 µL of 100 nM DNA template [2] (final concentration, 10 nM), 2 µL of 400 nM DNA template [1] (final concentration, 40 nM), 2 µL of 120 nM Detection Probe [1] (final concentration, 12 nM), 2 µL of water or 120 nM Capture Probe [1] (final concentration, 12 nM), 2 µL of 480 nM DNA primer [1] (final concentration, 48 nM), 2 µL of 10×attached buffer, 1 µL of 20×attached BSA solution, 2 µL of 10 mM dNTPs (final concentration, 1 mM), 1 µL of 200 mM KCl solution (final concentration, 10 mM), 2 µL of 1 U/µL Phi29 Polymerase (final concentration, 0.1 U/µL), and 2 µL of 10 nM thrombin (Thr) (20 µL in total).

Preparation of b1 and b2 of FIG. 5

A mixture was prepared with 2 µL of 100 nM DNA template [2] (final concentration, 10 nM), 2 µL of 400 nM DNA template [1] (final concentration, 40 nM), 2 µL of 120 nM Detection Probe [1] (final concentration, 12 nM), 2 µL of water or 120 nM Capture Probe [1] (final concentration, 12 nM), 2 µL of 480 nM DNA primer [1] (final concentration, 48 nM), 2 µL of 10×attached buffer, 1 µL of 20×attached BSA solution, 2 µL of 10 mM dNTPs (final concentration, 1 mM), 1 µL of 200 mM KCl solution (final concentration, 10 mM), 2 μL of 1 U/μL Phi29 Polymerase (final concentration, 0.1 U/μL), and 2 μL of 10 nM lysozyme (Lys) (20 μL in total).

Preparation of c1 and c2 of FIG. 5

A mixture was prepared with 2 μL of 100 nM DNA template [2] (final concentration, 10 nM), 2 μL of 400 nM DNA template [1] (final concentration, 40 nM), 2 μL of 120 nM Detection Probe [1] (final concentration, 12 nM), 2 μL of water or 120 nM Capture Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of 10 nM lectin (Lec) (20 μL in total).

Preparation of d1 and d2 of FIG. 5

A mixture was prepared with 2 μL of 100 nM DNA template [2] (final concentration, 10 nM), 2 μL of 400 nM DNA template [1] (final concentration, 40 nM), 2 μL of 120 nM Detection Probe [1] (final concentration, 12 nM), 2 μL of water or 120 nM Capture Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of 10 nM streptavidin (SA) (20 μL in total).

Preparation of e1 and e2 of FIG. 5

A mixture was prepared with 2 μL of 100 nM DNA template [2] (final concentration, 10 nM), 2 μL of 400 nM DNA template [1] (final concentration, 40 nM), 2 μL of 120 nM Detection Probe [1] (final concentration, 12 nM), 2 μL of water or 120 nM Capture Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of water (20 μL in total).

Example 1-3

Thrombin Detection Method Using Split Aptamer (Confirmation of Reaction Progress with Protein Mixed Solution)

Figure 6:
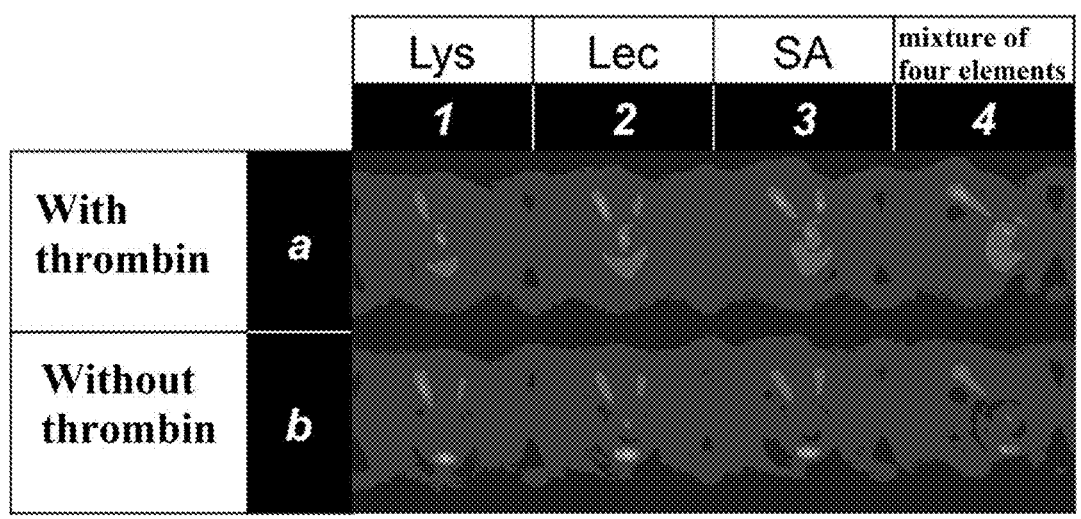
FIG. 6 is a diagram (photographs) illustrating results of detection of thrombin in Example 1-3.

Preparation of a1 to a4 of FIG. 6

A mixture was prepared with 2 μL of 100 nM DNA template [2] (final concentration, 10 nM), 2 μL of 400 nM DNA template [1] (final concentration, 40 nM), 2 μL of 120 nM Detection Probe [1] (final concentration, 12 nM), 2 μL of water or 120 nM Capture Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of a target solution (a mixture of two substances: thrombin/lysozyme Lys, thrombin/lectin Lec, or thrombin/streptavidin SA; or a mixture of four substances: thrombin/Lys, Lec, SA) (20 μL in total).

Preparation of b1 to b4 of FIG. 6

A mixture was prepared with 2 μL of 100 nM DNA template [2] (final concentration, 10 nM), 2 μL of 400 nM DNA template [1] (final concentration, 40 nM), 2 μL of 120 nM Detection Probe [1] (final concentration, 12 nM), 2 μL of water or 120 nM Capture Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of a 10 nM target solution (lysozyme Lys; lectin Lec; streptavidin SA; or a mixture of three substances: Lys, Lec, SA) (20 μL in total).

Example 2-1

Streptomycin Detection Method Using Split Aptamer

Figure 8:
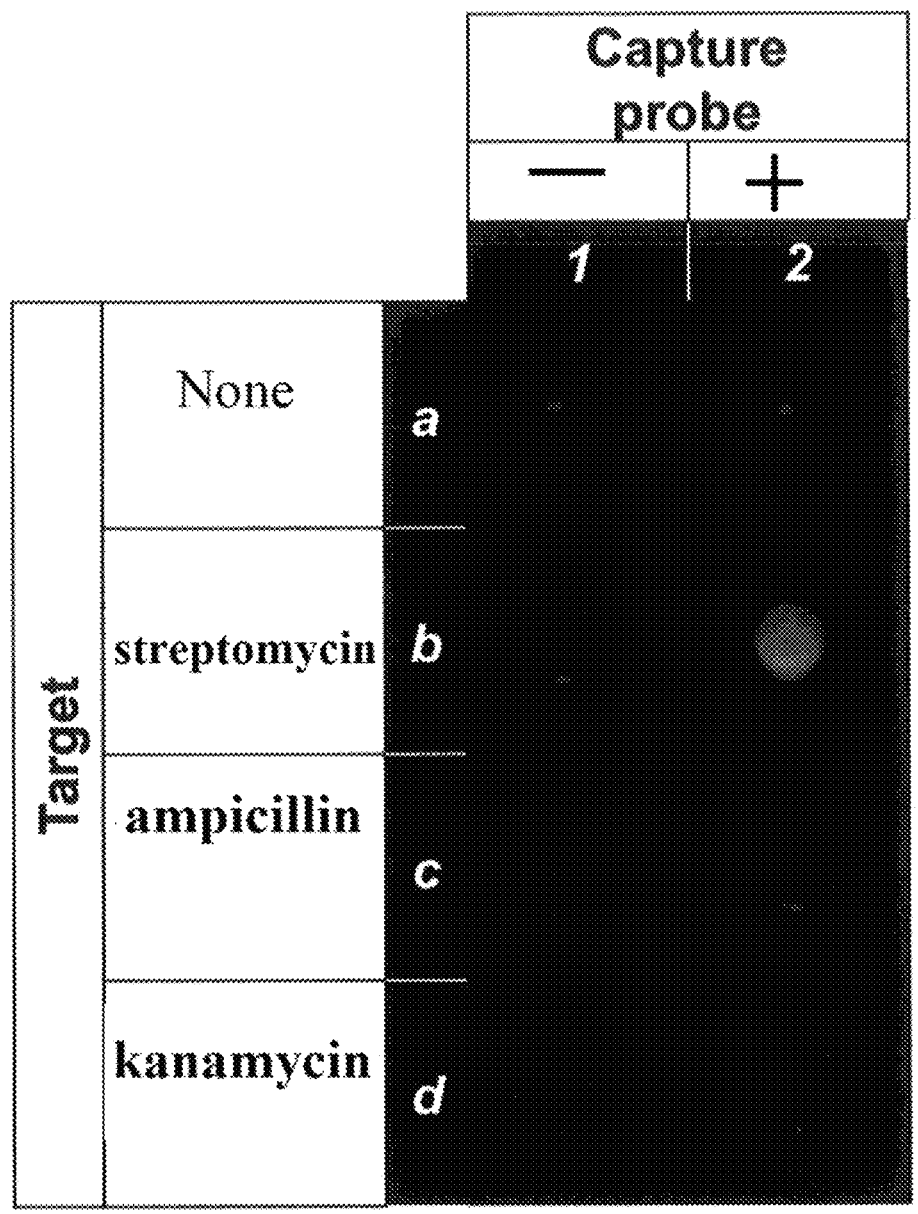
FIG. 8 is a diagram (photographs) illustrating results of detection of streptomycin in Example 2-1.

Preparation of a1 and a2 of FIG. 8

A mixture was prepared with 2 μL of 100 nM DNA template [2] (final concentration, 10 nM), 2 μL of 400 nM DNA template [1] (final concentration, 40 nM), 2 μL of 120 nM Detection Probe [2] (final concentration, 12 nM), 2 μL of water or 120 nM Capture Probe [2] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of water (20 μL in total).

Preparation of b1 and b2 of FIG. 8

A mixture was prepared with 2 μL of 100 nM DNA template [2] (final concentration, 10 nM), 2 μL of 400 nM DNA template [1] (final concentration, 40 nM), 2 μL of 120 nM Detection Probe [2] (final concentration, 12 nM), 2 μL of water or 120 nM Capture Probe [2] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of 1 mM streptomycin (final concentration, 100 μM) (20 μL in total).

Preparation of c1 and c2 of FIG. 8

A mixture was prepared with 2 μL of 100 nM DNA template [2] (final concentration, 10 nM), 2 μL of 400 nM DNA template [1] (final concentration, 40 nM), 2 μL of 120 nM Detection Probe [2] (final concentration, 12 nM), 2 μL of water or 120 nM Capture Probe [2] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of 1 mM ampicillin (final concentration, 100 μM) (20 μL in total).

Preparation of d1 and d2 of FIG. 8

A mixture was prepared with 2 μL of 100 nM DNA template [2] (final concentration, 10 nM), 2 μL of 400 nM DNA template [1] (final concentration, 40 nM), 2 μL of 120 nM Detection Probe [2] (final concentration, 12 nM), 2 μL of water or 120 nM Capture Probe [2] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 200 mM KCl solution (final concentration, 10 mM), 2 μL of 1 U/μL Phi29 Polymerase (final concentration, 0.1 U/μL), and 2 μL of 1 mM kanamycin (final concentration, 100 μM) (20 μL in total).

Example 2-2

Figure 9:
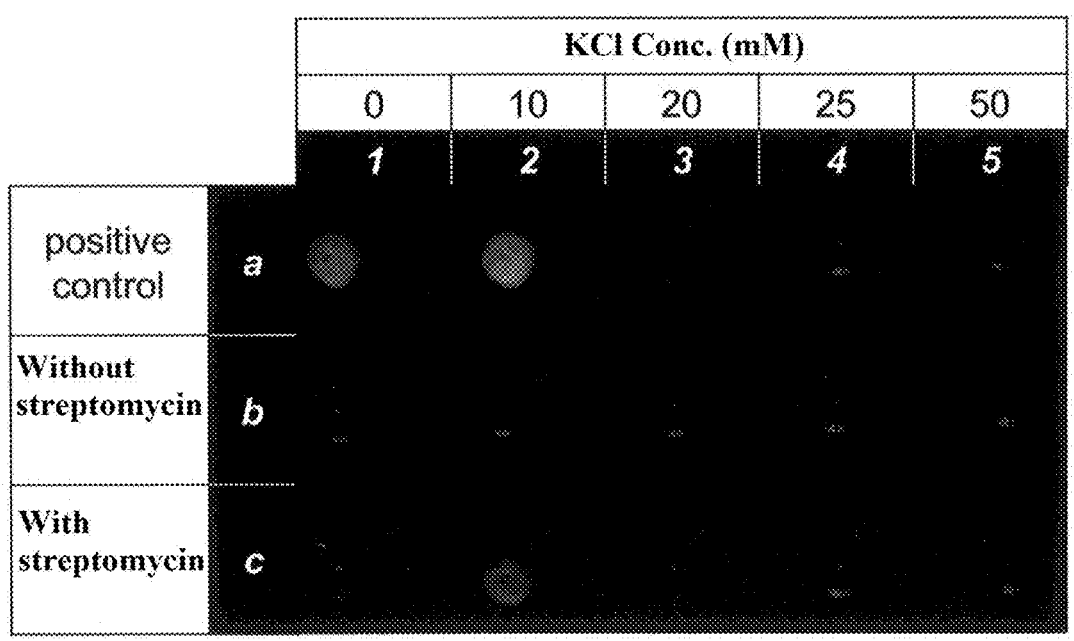
FIG. 9 is a diagram (photographs) illustrating results of detection of streptomycin in Example 2-2.

Streptomycin Detection Method Using Split Aptamer (Study on Salt Concentration)
Preparation of a1 to a5 of FIG. 9
A mixture was prepared with 2 μL of 100 nM DNA template [2] (final concentration, 10 nM), 2 μL of 400 nM DNA template [1] (final concentration, 40 nM), 2 μL of 120 nM Capture Probe [1] (final concentration, 12 nM), 2 μL of 120 nM Detection Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 0 to 1000 mM KCl solution (final concentration, 0 to 50 mM), 2 μL of 1 U/μL Phi29 Polymerase (final concentration, 0.1 U/μL), and 2 μL of 1 mM streptomycin (final concentration, 100 μM) (20 μL in total).

TABLE 1

Sequences of Oligonucleotides

| | length (mer) | Sequence (5'→3') | Modification |
|---|---|---|---|
| DNA primer [1] | 18 | GAAGCTGTTGTTATCACT (SEQ ID NO: 7) | |
| Positive control primer | 30 | AGCTCCTTTTTTGGGACTTTTCTTCTTCGA (SEQ ID NO: 8) | |
| Capture Probe [1] | 31 | AAAGGAGAAGCTCAAGCTCTTTTGGTTGGTG (SEQ ID NO: 9) | 3'-end phosphorylated |
| Capture Probe [2] | 37 | AAAGGACAACCTCAAGCTCCggcaccacggu cggauc (SEQ ID NO: 10) | 3'-end phosphorylated |
| Detection probe [1] | 17 | TGGTTGGAAATTTTTG (SEQ ID NO: 11) | |
| Detection probe [2] | 28 | gaucgcauuuggacuucugccTTTTTTG (SEQ ID NO: 12) | |
| DNA template [1] | 62 | CCCAACCCTACCCACCCTCAAGAAAAAAAAG TGATAATTGTTGTCGAAGAAGAAAAAAAATT (SEQ ID NO: 13) | circulated |
| DNA template [2] | 67 | CCCAAAAAAGGAGCTTGAGGTTCTCCTTTAA AAAGAAGCTGTTGTATTGTTGTCGAAGATGA AAAGT (SEQ ID NO: 14) | circulated |

Note 1:
The upper-case letters indicate DNA, and the lower-case letters indicate RNA.
Note 2:
Each double-stranded DNA was prepared by annealing with its complementary strand.

DNA template [1] (final concentration, 40 nM), 2 μL of 120 nM Positive control Primer (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 0 to 1000 mM KCl solution (final concentration, 0 to 50 mM), 2 μL of 1 U/μL Phi29 Polymerase (final concentration, 0.1 U/μL), and 4 μL of water (20 μL in total).
Preparation of b1 to b5 of FIG. 9
A mixture was prepared with 2 μL of 100 nM DNA template [2] (final concentration, 10 nM), 2 μL of 400 nM DNA template [1] (final concentration, 40 nM), 2 μL of 120 nM Capture Probe [1] (final concentration, 12 nM), 2 μL of 120 nM Detection Probe [1] (final concentration, 12 nM), 2 μL of 480 nM DNA primer [1] (final concentration, 48 nM), 2 μL of 10×attached buffer, 1 μL of 20×attached BSA solution, 2 μL of 10 mM dNTPs (final concentration, 1 mM), 1 μL of 0 to 1000 mM KCl solution (final concentration, 0 to 50 mM), 2 μL of 1 U/μL Phi29 Polymerase (final concentration, 0.1 U/μL), and 2 μL of water (20 μL in total).
Preparation of c1 to c5 of FIG. 9
A mixture was prepared with 2 μL of 100 nM DNA template [2] (final concentration, 10 nM), 2 μL of 400 nM Reagents Used:
ThT (thioflavin T) derivative
5×PBS153NM
50 mM $HPO_4^{2-}$, 730 mM $Cl^-$, 765 mM $Na^+$, 13.5 mM $K^+$, 12.5 mM $Mg^{2+}$; pH 7.4
1×PBS153NM
10 mM $HPO_4^{2-}$, 146 mM $Cl^-$, 153 mM $Na^+$, 2.7 mM $K^+$, 2.5 mM $Mg^{2+}$; pH 7.4
Polymerase Reaction
The solutions prepared as described above were incubated at 37° C. for 2 hours.
Detection
To 8 μL of the solution after the polymerase reaction, 2 μL of 5×PBS153NM buffer was added.
With 10 μL of the mixed solution, 2 μL of a fluorescent dye (30 μM ThT derivative solution in 1×PBS153NM buffer; final concentration (5 μM)) was mixed, and then the resulting mixture was incubated at 25° C. for 30 minutes.
The prepared solution was subjected to irradiation using a 410-nm UV lamp. A photograph was taken with a camera equipped with a cut-off filter (which cuts off wavelengths shorter than 460 nm).

<Results>

Example 1

Thrombin Detection Method Using Split Aptamer

This method is a method for detecting a protein present in a body.

Figure 3:
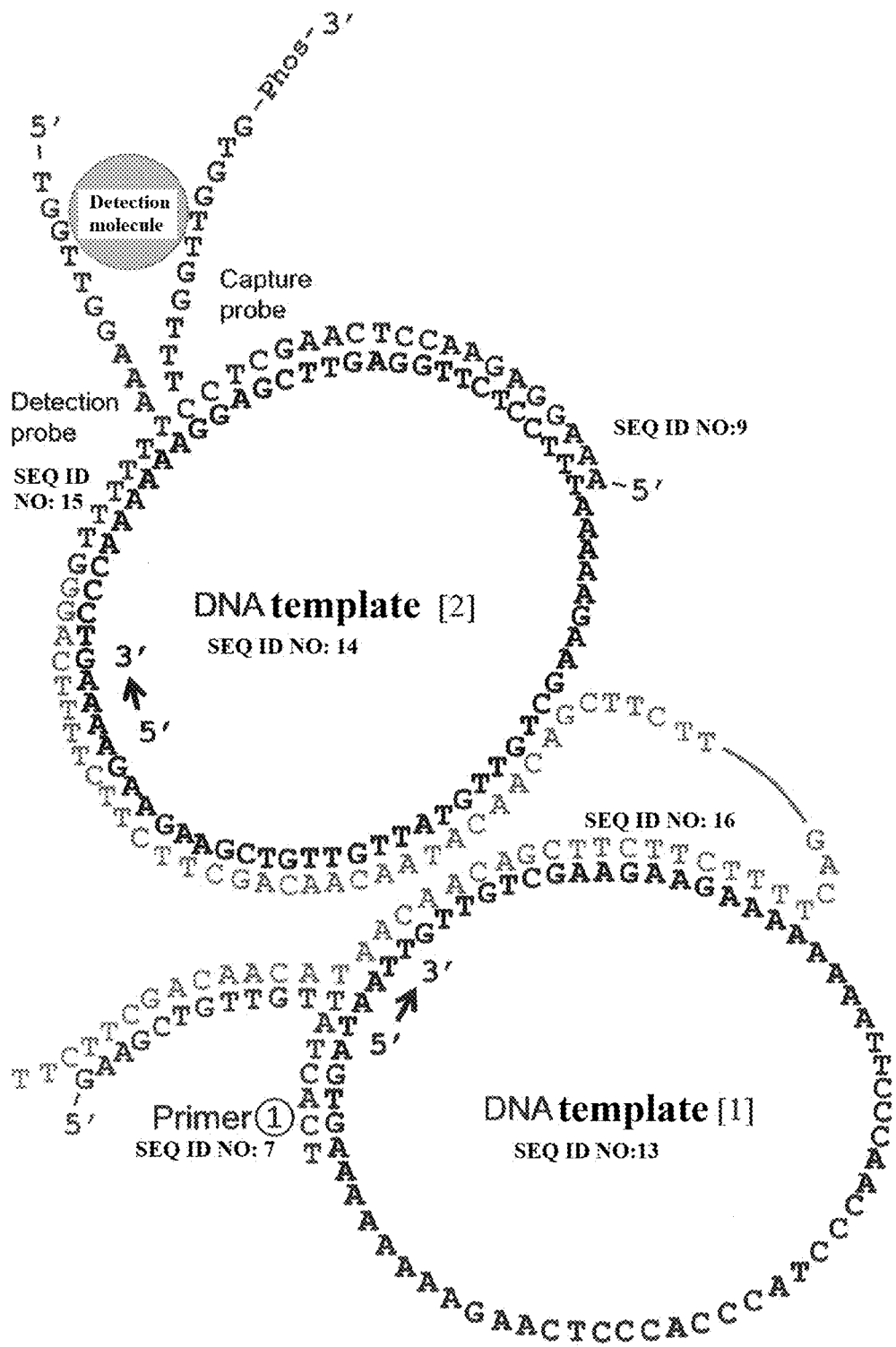
FIG. 3 is a diagram illustrating formation of a complex of thrombin, a capture oligonucleotide, a first single-stranded circular DNA, and an oligonucleotide primer (detection probe), and formation of a complex of its extension product, a second single-stranded circular DNA, and a second primer, in Example 1.

In this experiment, thrombin was targeted. As thrombin-detecting portions, a split aptamer was used. The design was as shown in FIG. 3.

Since the aptamer forms a higher order structure to bind to thrombin, a study was carried out on the salt concentration. In cases where the salt concentration is too low, the higher order structure of the aptamer cannot be formed, while at high salt concentration, the RCA reaction is inhibited.

As shown in FIGS. 4 a1 to a5, the progress of the RCA reaction was studied. As a result, it was found that the progress of the reaction is not affected when the salt concentration is not more than 10 mM, and that the progress is inhibited when the salt concentration is higher than this. Further, while the reaction did not proceed at a salt concentration of 0 mM as shown in FIG. 4 c1, the reaction proceeded at 10 mM as shown in FIG. 4 c2. At salt concentrations higher than this (FIGS. 4 c3 to 5), no progress of the reaction was found.

From the results in FIG. 5, it was found that proteins other than thrombin allow the reaction to proceed, and that the reaction is specific only to thrombin. Further, from the results in FIG. 6, it was found that, even in the presence of contamination with various proteins, the reaction proceeds as long as thrombin is present.

Example 2

Streptomycin Detection Method Using Split Aptamer

This method is a method for detecting a small molecule.

Figure 7:
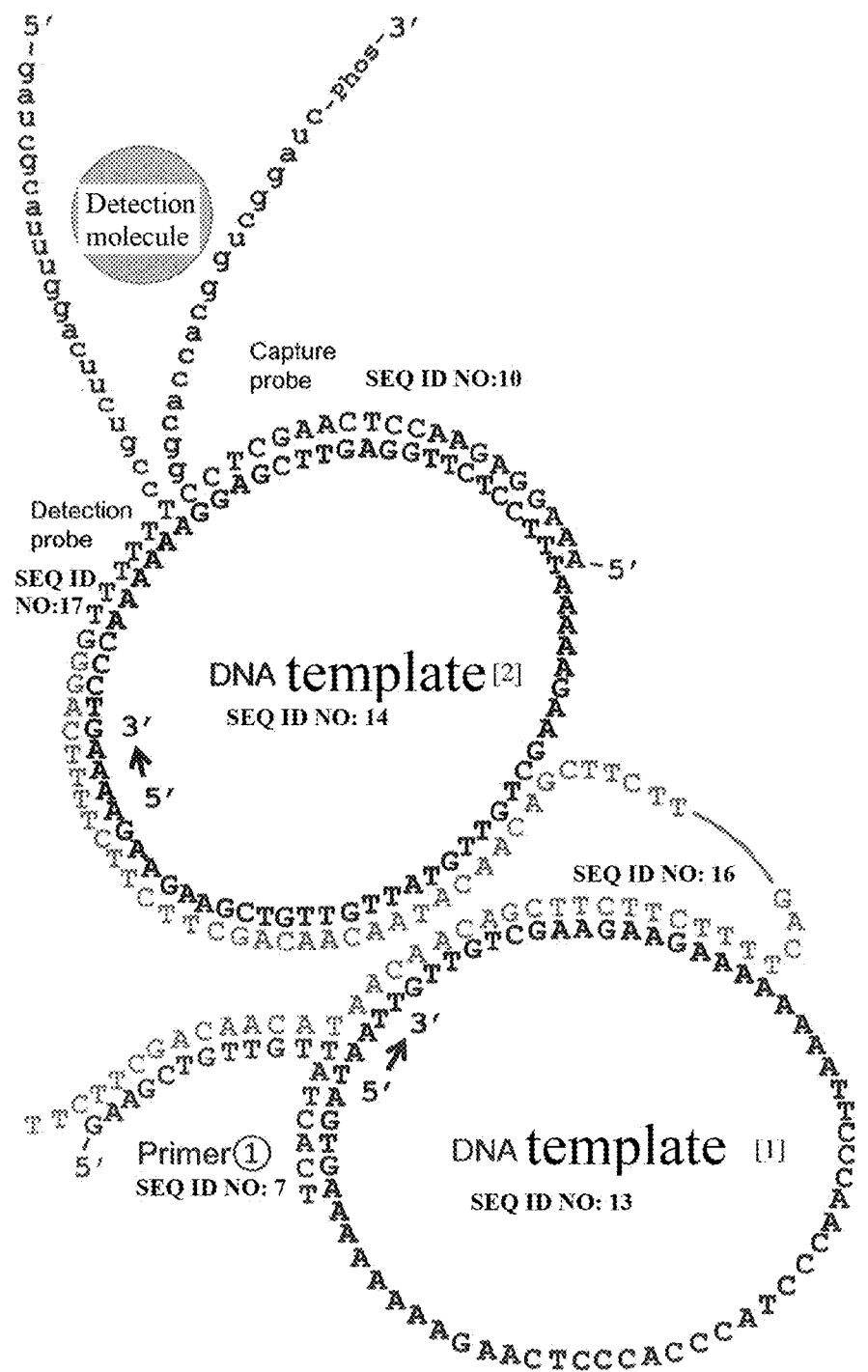
FIG. 7 is a diagram illustrating formation of a complex of streptomycin, a capture oligonucleotide, a first single-stranded circular DNA, and an oligonucleotide primer (detection probe), and formation of a complex of its extension product, a second single-stranded circular DNA, and a second primer, in Example 2. The upper-case letters indicate DNA, and the lower-case letters indicate RNA.

In this experiment, the antibiotic streptomycin was targeted. As streptomycin-detecting portions, a split aptamer was used. The design was as shown in FIG. 7.

In the present experiment, whether specific detection is possible or not was studied not only for streptomycin, but also for ampicillin and kanamycin.

As a result, it was found that specific detection is possible only for streptomycin (FIG. 8 b1).

Subsequently, the salt concentration in the reaction was studied. The aptamer forms a higher order structure to bind to streptomycin, and, in cases where the salt concentration is too low, the formation of the higher order structure by the aptamer may be impossible. On the other hand, at high salt concentration, the RCA reaction may be inhibited.

As shown in FIGS. 9 a1 to a5, the progress of the RCA reaction was studied. As a result, it was found that the progress of the reaction is not affected when the salt concentration is not more than 10 mM, and that the progress is inhibited when the salt concentration is higher than this. Further, while the reaction did not proceed at a salt concentration of 0 mM as shown in FIG. 9 c1, the reaction proceeded at 10 mM as shown in FIG. 9 c2. At salt concentrations higher than this (FIGS. 9 c3 to 5), no progress of the reaction was found.

DESCRIPTION OF SYMBOLS

10 . . . Single-stranded circular DNA;
11 . . . capture oligonucleotide;
12 . . . oligonucleotide primer;
13 . . . amplification product (elongated chain);
14 . . . target molecule;
15 . . . guanine quadruplex detection reagent;
101 . . . first region (primer-binding sequence);
102 . . . second region;
103 . . . sequence complementary to guanine quadruplex-forming sequence;
111 . . . sequence complementary to second region;
112 . . . second aptamer sequence;
121 . . . first aptamer sequence;
122 . . . sequence complementary to first region;
131 . . . sequence containing guanine quadruplex.
20 . . . Single-stranded circular DNA;
21 . . . capture oligonucleotide;
22 . . . first oligonucleotide primer;
23 . . . first amplification product (elongated chain);
24 . . . second single-stranded circular DNA;
25 . . . second oligonucleotide primer;
26 . . . second amplification product (elongated chain);
27 . . . target molecule;
28 . . . guanine quadruplex detection reagent;
201 . . . first region (primer-binding sequence);
202 . . . second region;
203 . . . sequence complementary to second-single-stranded-circular-DNA-binding sequence;
204 . . . region adjacent to 5'-side of 203;
211 . . . sequence complementary to second region;
212 . . . second aptamer sequence;
221 . . . first aptamer sequence;
222 . . . sequence complementary to first region;
231 . . . region complementary to 203;
232 . . . region complementary to region 204;
241 . . . sequence identical to sequence 203 complementary to second-single-stranded-circular-DNA-binding sequence;
242 . . . second primer-binding sequence;
243 . . . sequence complementary to guanine quadruplex-forming sequence;
251 . . . sequence identical to region 204;
252 . . . sequence complementary to second primer-binding sequence 242 of second single stranded circular DNA;
261 . . . sequence containing guanine quadruplex.

The invention claimed is:

1. A method of detecting a target molecule, comprising:
   forming a complex of a target molecule, a capture oligonucleotide, an oligonucleotide primer, and a single-stranded circular DNA;
   performing a nucleic acid amplification reaction by rolling circle amplification based on the formation of the complex; and
   detecting amplified nucleic acid;
   wherein
   the single-stranded circular DNA contains a first region, and a second region linked to the 3'-side of the first region;
   the oligonucleotide primer contains a first aptamer sequence which binds to the target molecule, and a sequence which is linked to the 3'-side of the first aptamer sequence and is complementary to the first region of the single-stranded circular DNA; and
   the capture oligonucleotide contains a sequence complementary to the second region of the single-stranded circular DNA, and a second aptamer sequence which is linked to the 3'-side of the sequence complementary to the second region and binds to the target molecule.

2. The method of detecting a target molecule according to claim 1, wherein the single-stranded circular DNA further contains a sequence complementary to a detection reagent-binding sequence.

3. A method of detecting a target molecule, comprising:
   forming a first complex containing a target molecule, a capture oligonucleotide, a first oligonucleotide primer, and a first single-stranded circular DNA;
   performing a nucleic acid amplification reaction by rolling circle amplification based on the formation of the first complex;
   hybridizing a second single-stranded circular DNA and a second oligonucleotide primer with an elongated chain generated by the nucleic acid amplification reaction, to form a second complex containing the elongated chain, the second primer, and the second single-stranded circular DNA;

performing a nucleic acid amplification reaction by rolling circle amplification based on the formation of the second complex; and detecting amplified nucleic acid;

wherein the first single-stranded circular DNA contains a first region, a second region linked to the 3'-side of the first region, and a sequence complementary to a second-single-stranded-circular-DNA-binding sequence;

the first oligonucleotide primer contains a first aptamer sequence which binds to the target molecule, and a sequence which is linked to the 3'-side of the first aptamer sequence and is complementary to the first region of the first single-stranded circular DNA;

the capture oligonucleotide contains a sequence complementary to the second region of the first single-stranded circular DNA, and a second aptamer sequence which is linked to the 3'-side of the sequence complementary to the second region and binds to the target molecule;

the second single-stranded circular DNA contains the sequence identical to the sequence complementary to the second-single-stranded-circular-DNA-binding sequence in the first single-stranded circular DNA, a second oligonucleotide primer-binding sequence adjacent to the 5'-side of said sequence, and a sequence complementary to a detection reagent-binding sequence; and the second oligonucleotide primer contains the sequence identical to the sequence complementary to a region adjacent to the 5'-side of the second-single-stranded-circular-DNA-binding sequence in the first single-stranded circular DNA, and a sequence which is adjacent to the 3'-side of said sequence and is complementary to the second primer-binding sequence in the second single-stranded circular DNA.

4. The method of detecting a target molecule according to claim 2, wherein the detection reagent-binding sequence is a guanine quadruplex-forming sequence, and the detection reagent is a guanine quadruplex-binding reagent.

5. The method of detecting a target molecule according to claim 4, wherein the sequence complementary to the guanine quadruplex-forming sequence contains a $C_3N_{1-10}C_3N_{1-10}C_3N_{1-10}C_3$ sequence.

6. The method of detecting a target molecule according to claim 4, wherein the guanine quadruplex-binding reagent contains a compound represented by the following General Formula (I):

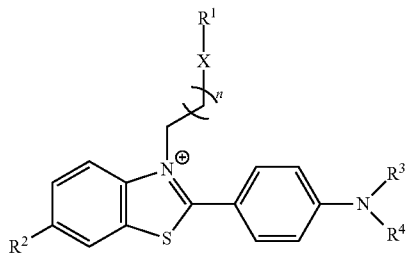

wherein
R$^1$ represents hydrogen, or a hydrocarbon group optionally containing one or more selected from the group consisting of O, S, and N;
R$^2$, R$^3$, and R$^4$ each independently represent a C$_1$-C$_5$ hydrocarbon group;

n represents an integer of 0 to 5; and
X represents O, S, or NH.

7. The method of detecting a target molecule according to claim 1, wherein the target molecule is a protein, a peptide, or a low molecular weight compound.

8. A reagent for detecting a target molecule, the reagent comprising:

a single-stranded circular DNA containing a first region, and a second region linked to the 3'-side of the first region;

an oligonucleotide primer containing a first aptamer sequence which binds to the target molecule, and a sequence which is linked to the 3'-side of the first aptamer sequence and is complementary to the first region of the single-stranded circular DNA; and a capture oligonucleotide containing a sequence complementary to the second region of the single-stranded circular DNA, and a second aptamer sequence which is linked to the 3'-side of the sequence complementary to the second region and binds to the target molecule.

9. The reagent for detecting a target molecule according to claim 8, wherein the single-stranded circular DNA further contains a sequence complementary to a detection reagent-binding sequence.

10. The reagent for detecting a target molecule according to claim 9, wherein the detection reagent-binding sequence is a guanine quadruplex-forming sequence.

11. The reagent for detecting a target molecule according to claim 10, further comprising a guanine quadruplex-binding reagent.

12. The method of detecting a target molecule according to claim 3, wherein the detection reagent-binding sequence is a guanine quadruplex-forming sequence, and the detection reagent is a guanine quadruplex-binding reagent.

13. The method of detecting a target molecule according to claim 12, wherein the sequence complementary to the guanine quadruplex-forming sequence contains a $C_3N_{1-10}C_3N_{1-10}C_3N_{1-10}C_3$ sequence.

14. The method of detecting a target molecule according to claim 13, wherein the guanine quadruplex-binding reagent contains a compound represented by the following General Formula (I):

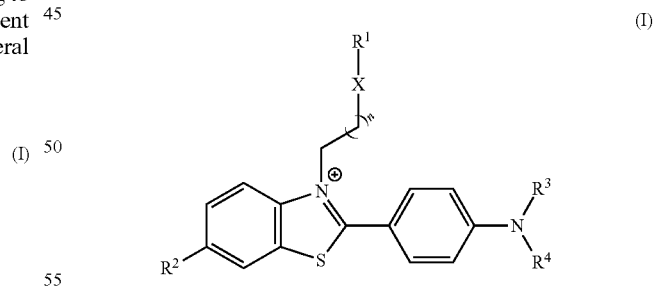

wherein
R$^1$ represents hydrogen, or a hydrocarbon group optionally containing one or more selected from the group consisting of O, S, and N;
R$^2$, R$^3$, and R$^4$ each independently represent a C$_1$-C$_5$ hydrocarbon group;
n represents an integer of 0 to 5; and
X represents O, S, or NH.

15. The method of detecting a target molecule according to claim 3, wherein the target molecule is a protein, a peptide, or a low molecular weight compound.

16. A reagent for detecting a target molecule, the reagent comprising:
- a first single-stranded circular DNA which contains a first region, a second region linked to the 3'-side of the first region, and a sequence complementary to a second-single-stranded-circular-DNA-binding sequence;
- a first oligonucleotide primer which contains a first aptamer sequence which binds to the target molecule, and a sequence which is linked to the 3'-side of the first aptamer sequence and is complementary to the first region of the first single-stranded circular DNA;
- a capture oligonucleotide which contains a sequence complementary to the second region of the first single-stranded circular DNA, and a second aptamer sequence which is linked to the 3'-side of the sequence complementary to the second region and binds to the target molecule;
- a second single-stranded circular DNA which contains the sequence identical to the sequence complementary to the second-single-stranded-circular-DNA-binding sequence in the first single-stranded circular DNA, a second oligonucleotide primer-binding sequence adjacent to the 5'-side of said sequence, and a sequence complementary to a detection reagent-binding sequence; and
- a second oligonucleotide primer which contains the sequence identical to the sequence complementary to a region adjacent to the 5'-side of the second-single-stranded-circular-DNA-binding sequence in the first single-stranded circular DNA, and a sequence which is adjacent to the 3'-side of said sequence and is complementary to the second primer-binding sequence in the second single-stranded circular DNA.

17. The reagent for detecting a target molecule according to claim 16, wherein the detection reagent-binding sequence is a guanine quadruplex-forming sequence.

18. The reagent for detecting a target molecule according to claim 17, further comprising a guanine quadruplex-binding reagent.

* * * * *